United States Patent [19]

Staub et al.

[11] Patent Number: 4,849,219

[45] Date of Patent: Jul. 18, 1989

[54] MICROBICIDES

[75] Inventors: Theodor Staub, Riehen; Robert J. Williams, Schönenbuch; Paul Margot, Biel-Benken, all of Switzerland

[73] Assignee: Ciba-Geigy Corporation, Ardsley, N.Y.

[21] Appl. No.: 188,108

[22] Filed: Apr. 27, 1988

Related U.S. Application Data

[63] Continuation of Ser. No. 941,455, Dec. 12, 1986, abandoned.

[30] Foreign Application Priority Data

Dec. 16, 1985 [CH] Switzerland .................. 5406/85

[51] Int. Cl.$^4$ ............... A01N 37/12; A01N 37/44; A01N 43/76; A01N 59/26
[52] U.S. Cl. ..................... 424/605; 514/150; 514/374; 514/378; 514/472; 514/538; 424/601; 424/604; 424/606; 424/602
[58] Field of Search .................. 424/128; 514/538

[56] References Cited

U.S. PATENT DOCUMENTS

| | | | |
|---|---|---|---|
| 4,075,324 | 2/1978 | Thizy et al. | 424/128 |
| 4,151,299 | 4/1979 | Hubele | 514/538 |
| 4,507,310 | 3/1985 | Devoise-Lambert et al. | 514/376 |

FOREIGN PATENT DOCUMENTS 2095114 9/1982 United Kingdom .

OTHER PUBLICATIONS

C.A., 103:49639z, Bower et al.
C.A., 102:199,454d, Rohrback et al.

*Primary Examiner*—Allen J. Robinson
*Attorney, Agent, or Firm*—Edward McC. Roberts

[57] ABSTRACT

A microbicidal composition comprising at least one microbicidal acylaniline derivative such as metalaxyl, furalaxyl and the like, and $H_3PO_3$ or a salt thereof, exerts a synergistically potentiated activity against plant diseases, especially also against acylaniline-resistant pathogens. The composition may optionally comprise a third protective fungicidal component. The three active components may be applied in succession in any order or simultaneously.

9 Claims, No Drawings

MICROBICIDES

This application is a continuation of application Ser. No. 941,455, filed Dec. 12, 1986, now abandoned.

The present invention relates to microbicidal compositions with enhanced synergistic activity against plant diseases and to a method of using such compositions. In recent years, the development of pesticides capable of effectively controlling oomycetes, especially the downy mildew species (Peronosporales), and of preventing attack at the first onset, has been processing space. The most prominent chemical group of effective pesticides originates from the fungicidal acylanilines (group I herein). The great advantage of these compounds is their systemic activity. By virtue of their ability to penetrate into the plant cells and sap-flow, they are able to protect these in all parts against fungus attack or to prevent the spread of fungal growth at the onset of attack.

However, the exceedingly intensive use of acylanilines over the past 10 years has led to the unexpectedly rapid growth of resistance to these fungicides. For this reason, recourse has been had to long-established protective fungicides in order to slow down or, where it has not yet occurred in specific crops, to prevent, the development of resistance to acylanilines by combining said fungicides with acylanilines or applying them alternately.

The following protective fungicides have been proposed as mixture components for acylanilines of formula I or as commercially available:

copper salts (e.g. $CuSO_4$, copper(II) chloride or copper(II) oxychloride,
zinc ethylene bis(dithiocarbamate) (zineb),
manganese(II) ethylene bis(dithiocarbamate) (maneb),
zinc 1,2-propylene bisdithiocarbamate (propineb),
manganese(II) zinc bis(dithiocarbamate) (mancozeb),
N-(trichloromethylthio)phthalimide (folpet),
N-(trichloromethylthio)-4-cyclohexene-1,2-dicarboximide (captan),
N-(1,1,2,2-tetrachloroethylthio)-4-cyclohexene-1,2-dicarboximide (captafol),
2,4,5,6-tetrachloroisophthalonitrile (chlorothalonil),
1,4-dithiaanthraquinone-2,3-dicarbonitrile (dithianone),
N-dichlorofluoromethylthio-N',N'-dimethyl-N-phenyl-sulfamide (dichlofuanide),
1,4-dichloro-2,5-dimethoxybenzene (chloroneb),
3-hydroxy-5-methylisoxazole (hymexazole).

These and other protective leaf fungicides are obvious mixture components to the skilled person. By copper salts are meant all copper salts that are commonly employed in "Bordeaux mixtures" in viticulture.

The present invention solves the problem of overcoming resistance and of effectively controlling oomycetes, as well as of controlling other plant diseases in another manner. The present invention relates to a mixture comprising ($\alpha$) an acylaniline of group I

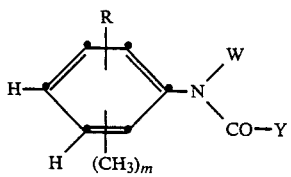  (I)

wherein

R is methyl, chlorine, nitro or azido ($N_3$),
W is the $\alpha$-methylpropionate group —C($CH_3$)COOCH$_3$ or the heterocyclic ring

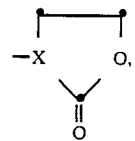

wherein X is either CH or N,
Y is a group selected from —$CH_2$—O—$CH_3$ (methoxymethyl), —$CH_2Cl$ (chloromethyl),

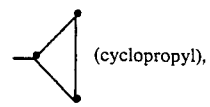 (cyclopropyl),

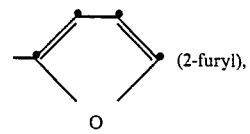 (2-furyl),

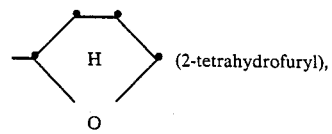 (2-tetrahydrofuryl),

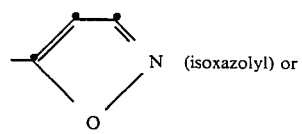 (isoxazolyl) or

—$CH_2$—$C_6H_5$ (benzyl) and
m is 1 or 2, or may also be 0, if R is a chlorine atom in metaposition with respect to the amino group and W is at the same time a butyrolactone ring (X=CH), and ($\beta$) a fungicide of group II comprising phosphorous acid ($H_3PO_3$) or an alkali metal salt, an alkaline earth metal salt or an unsubstituted or substituted ammonium salt thereof, or the zinc, copper, nickel or manganese salt thereof.

In formula I above, the substituent R can be in position 2, 3 or 6 of the phenyl ring. If available, the $CH_3$ group can also be in one or two of these positions. A $NO_2$ substituent is preferably in 3-position if W is an $\alpha$-methylpropionate group. Alkali metal salts of phosphorous acid will be understood as meaning all monobasic or dibasic salts $MeH_2PO_3$ or $Me_2HPO_3$, wherein Me is lithium, sodium or potassium or also mixed salts of these three ions. By ammonium salts are meant the above mentioned phosphites, wherein Me is either $NH_4^+$ or an $NH_4^+$ cation which is substituted by 1 to 4 aliphatic and/or aromatic radicals, e.g. $[NH_3—C_2H_5]^+$, $[N(CH_3)_4]^+$, $[N(CH_3)_3Ph]^+$, $[NH_2CH_3(C_6H_4Cl)]^+$, $[NH_2(isoC_3H_7)_2]^+$ and the like. Me can also stand for mixtures of alkali metal and ammonium salts.

By analogy, alkaline earth metal salts of phosphorous acid will be understood as meaning phosphites which contain calcium, magnesium, barium or strontium as caton and which are able to form mixed salts with one another or with alkali metal or ammonium cations.

Phosphorous acid and salts thereof were already proposed in 1975 (e.g. DE-24 53 401 or FR-2 252 056) for controlling fungal diseases in plant protection, but have so far not been used in actual practice. The principal reason is doubtless the phytotoxicity of $H_3PO_3$ and also of its salts. At the concentrations of 200–500 g/h necessary for an effective control of plant diseases in spray mixtures and which are needed for a really permanent reduction of fungus attack to less than 5 %, most crop plants suffer unacceptable damage which, at the least, retards plant growth during development and even causes parts of the plant to perish (e.g. by leaf necrosis).

It must therefore be regarded as entirely surprising that $H_3PO_3$ and salts thereof, i.e. the group II components mentioned above, in conjunction with the acylaniline fungicides of group I, exert three effects which are very useful in actual practice. Firstly, the fungicidal activity of a mixture of a compound of group I with a compound of group II is synergistically enhanced, i.e. to achieve a specific reduction of attack by disease, a substantially lower total amount of active ingredient is required. Secondly, at a total active ingredient concentration of 250 g a.i./ha or less, no phytotoxicity to crop plants is observed, especially to the sensitive vines. This effect is due in part to the reduction of the amount of $H_3PO_3$ or a salt thereof, but does not entirely explain why no toxicity at all is observed in the usual concentration range of 100 g–2000 g a.i./ha. Thirdly, such a combination of fungicides also completely controls strains of pathogens that are resistant to acylanilines of formula I.

Hence the present invention constitutes a substantial enrichment of the state of the art.

Preferred representatives of the fungicides of formula I are the following compounds, the majority of which are commercially available:

(1) methyl N-(2,6-dimethylphenyl)-N-(2-methoxyacetyl)-DL-alaninate (=metalaxyl),
(2) methyl N-(2,6-dimethylphenyl)-N-furoyl(2)-DL-alaninate (=furalaxyl),
(3) methyl N-(2-methyl-6-azidophenyl)-N-(2-methoxyacetyl)-DL-alaninate,
(4) methyl N-(2,3,6-trimethylphenyl)-N-(2-methoxyacetyl)-DL-alaninate,
(5) methyl N-(2,6-dimethylphenyl)-N-(phenylacetyl)-DL-alaninate (=benalaxyl);
(6 α-[N-(3-chlorophenyl)cyclopropanecarboxamido]-γ-butyrolactone (=cyprofuram),
(7) α-[N-(2,6-dimethylphenyl)chloromethylcarboxamido]-γ-butyrolactone (=ofurace),
(8) α-[N-(2,6-dimethylphenyl)methoxymethylcarboxamido]-γ-butyrolactone,
(9) α-[N-(2,3,6-trimethylphenyl)methoxymethylcarboxamido]-γ-butyrolactone,
(10) α-[N-(2,6-dimethyl-3-chlorophenyl)methoxymethylcarboxamido]-γ-butyrolactone,
(11) 2-methoxy-N-(2-oxo-1,3-oxazolidin-3-yl)-acet-2',6'-xylidine (=oxadixyl). The generically named fungicides are known to the skilled person from the literature. Compound 3 is known from EP patent specification 65 483 and compound 4 from U.S. Pat. No. 4,151,299. Compounds 8, 9 and 10 are disclosed in GB patent specification No. 1 577 702.

Further preferred representatives of group II compounds are a) phosphorous acid itself and the following salts:

(b) $NaH_2PO_3$, monosodium phosphite,
(c) $KH_2PO_3$, monopotassium phosphite,
(d) $Na_2HPO_3$, disodium phosphite,
(e) $K_2HPO_3$, dipotassium phosphite
(f) $(NH_4)H_2PO_3$, monoammonium phosphite,
(g) $Ca(H_2PO_3)_2$, monobasic calcium phosphite,
(h) $CaHPO_3$, dibasic calcium phosphite,
(i) $Ba(H_2PO_3)_2$, monobasic barium phosphite,
(j) $BaHPO_3$, dibasic barium phosphite,
(k) $MgHPO_3$, dibasic magnesium phosphite.
(l) $ZnHPO_3$, dibasic zinc phosphite,
(m) $Cu_2HPO_3$, dibasic copper(I) phosphite,
(n) $CuHPO_3$, dibasic copper(II) phosphite,
(o) $NiHPO_3$, dibasic nickel phosphite,
(p) $MnHPO_3$, manganese phosphite.

The above salts normally crystalline with one or more moles of water. If aqueuous spray mixtures or other aqueous formulations of the fungicide mixtures are used, the salts are in dissociated form with a phosphite ion $H[HPO_3]^-$ or $[HPO_3]^{2-}$. The alkaline earth metal cations can be hydrated. The choice of a salt of group II components for the preparation of fungicidal compositions depends on the extent to which the suitable phosphite ion can be made available for application to the plant or to parts therof. Owing to their water solubility, $H_3PO_3$ and the salts (b) to (h) are preferred. Barium salts and the other metal salts (k) to (p), as well as substituted ammonium salts of lower water solubility, are preferred whenever it is desired to avoid heavy dilution or washing off caused e.g. by rainfall. The Cu-phosphites (m) and (n) are particularly suitable mixture components.

Convenient mixture ratios of the two groups of components are: I:II=1:100 to 1:1, preferably I:II=1:25 to 1:1.

Depending on the component, especially preferred ratios are: I:II=1:8 to 2:3, e.g. I:II=1:7 or also I:II=1:4. The last mentioned three ratios are particularly advantageous for the more effective acylanilines, to which compounds (1), (3), (4), (8) and (9) belong. Irrespective, however, of whether they are individually more or less effective, the acylanilines of formula I, which are often classified in biological publications as "acylalanine funicides" on account of their uniform activity similar to that of their best known representative, metalaxyl, are subject to the generally identical potentiation of activity in the presence of $H_3PO_3$ or a salt thereof of formula II.

To the combinations which are preferred for use in actual practice belong the groups comprising the known commercial fungicides metalaxyl, furalaxyl, benalaxyl, cyprofuram, oruface and oxadixyl as well as compounds (9) and (10). Typical examples are combinations of these fungicides with $H_3PO_3$, $Na_2HPO_3$, copper phosphite or calcium phosphite, e.g. $Ca(H_2PO_3)_2.H_2O$. This last mentioned compound can also conveniently be used as anhydride and is then less rapidly washed off in wet weather conditions.

The active ingredient combinations of I+II of this invention have very useful curative, preventive and systemic properties for protecting cultivated plants. With these mixtures of formula I it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms. This also applies to microorganisms that have developed resistance to the so-called "acylalanine fungicides".

The combinations are effective against the phytopathogenic fungi belonging to the following classes: Ascomycetes (e.g. Venturia, Podosphaera, Erysiphe, Monilinia, Uncinula): Basidiomycetes (e.g. the genera Hemileia, Rhizoctonia, Puccinia); Fungi imperfecti (e.g. Botrytis, Helminthosporium, Fusarium, Septoria, Cercospora, Alternaria and, especially, Pyricularia). In addition, the compounds of formula I have a systemic action. They can also be used as seed dressing agents for protecting seeds (fruit, tubers, grains) and plant cuttings against fungus infections as well as against phytophathogenic fungi which occur in the soil. The combinations of the invention are especially well tolerated by plants and they are ecologically non-harmful. Phosphorus acid and its salts are converted in the course of time into phosphates and therefore act later as fertilisers, when applied to the soil. Acylanilines of formula I, in particular compound (1) to (4) and (8) to (10) are degraded and their presence in the soil is no longer detectable after one growing season.

Without implying any limitation, target crops to be protected within the scope of the present invention comprise e.g. the following species of plants:

cereals (wheat, barley, rye, oats, rice, sorghum and related crops), beet (sugar beet and fodder beet), drupes, pomes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers).

The combinations of the compounds of formulae I and II are normally applied in the form of compositions and can be applied to the crop area or plant to be treated, simultaneously or in succession, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a combination comprising at least one compound of formula I and one compound of formula II is application to the growing parts of plants, especially the leaves (foliar application). The number of applications and the rate of application depend on the biological and climatic life conditions of the pathogen. However, the active components can also penetrate the plant through the roots via the soil (systemic action) by drenching the locus of the plant with a liquid formulation, or by applying the compounds in solid form to the soil, e.g. in granular form (soil application). The compounds of formulae I and II may also be applied to seeds (coating) by impregnating the seed either with a liquid formulation of one component or coating them with a combined formulation. In special cases, further types of application are also possible, e.g. selective treatment of the buds or fruit.

The compounds of formulae I and II are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substanceas. As with the nature of the compositions, the methods of application, such as spraying, atomising, dusting, scattering, coating or pouring, are chosen in accordance with the intended objectives and the prevailing circumstances. Advantageous rates of application are normally from 100 g to 2 kg a.i./ha, most preferably from 100 g to 600 g a.i./ha.

The formulations are prepared in known manner, e.g. by homogeneously mixing and/or grinding the active inredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphtaic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as vegetable oils or epoxidised vegetables oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl choline, sphingomyeline, phosphatidyl inisotol, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphosphatidyl choline.

Depending on the nature of the compounds of formualae I and II to be formulated, suitable surface-active compounds are nonionic, cationic and/or anionic sufactants having good emulsifying, dispersing and wetting properties. The term "surfactants" will also be understood as comprising mixtures of surfactants.

Furthermore, the present invention also embraces a method of treating plant diseases, which comprises applying the compounds of formulae I and II and the compositions containing them to the locus already infected or in danger of infection. The application of both compounds I and II can be made in any order or simultaneously.

In the following Formulation Examples, the term "active ingredient" will be understood as meaning a combination of an acylaniline of group I with $H_3PO_3$ (or a salt thereof) of group II in the ratio 1:8 to 2:3. Throughout, percentages are by weight.

Where metalaxyl, furalaxyl, ofurace and oxadixyl are used, useful weight ratios of I:II (based on $H_3PO_3$) are 1:7; 1:5; 1:3; 3:5; 2:5 and 2:3.

| Wettable powders | (a) | (b) | (c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixtures is thoroughly ground in a suitable mill, affording wettable powders which can be diluted with water to give suspensions of the desired concentration.

| Emulsifiable concentrate | |
|---|---|
| active ingredient | 10% |
| octylphenol polyethlene glycol ether (4–5 moles of ethylene oxide) | 3% |
| calcium dodecylbenzenesulfonate | 3% |
| castor oil polyglycol ether (36 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| active ingredient | 5% | 8% |
| talcum | 95% | — |
| kaolin | — | 92% |

Ready-for-use dusts are obtained by mixing the active ingredient with the carriers, and grinding the mixture in a suitable mill.

| Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
|---|---|
| active ingredient | 3% |
| polyethylene glycol 200 (mol wt.) | 3% |
| kaolin | 94% |

The finely ground active ingredient is uniformly applied, in a mixer, to the kaolin moistened with polyethylene glycol. Non-dusty coated granulates are obtained in this manner.

BIOLOGICAL EXAMPLES (A) Action against Plasmopara viticola ("acylaniline resistant") on vines Residual-protective action Vine cuttings in the 6-8 leaf stage are sprayed with a spray mixture prepared from a wettable powder formulation of the test combination. After 24 hours, the treated plants are infected with a sporangia suspension of a fungus strain with dimished sensitivity to metalaxyl, ofurace and oxadixyl. Evaluation of fungus attack is made after incubation for 6 days at 95–100 % relative humidity and 20° C.

| Test combination | Spray mixture | | Fungus attack on 7th day |
|---|---|---|---|
| | % by weight | Ratio I:II | |
| metalaxyl | 0.006 | 1:7 | no visible attack |
| $Na_2HPO_3$ | 0.042 | | |
| metalaxyl | 0.0015 | 1:25 | no visible attack |
| $Na_2HPO_3$ | 0.0375 | | |
| metalaxyl | 0.005 | 1:4 | 0–5% |
| $H_3PO_3$ | 0.02 | | |
| ofurace | 0.005 | 1:3 | 5–10% |
| $Na_2HPO_3$ | 0.015 | | |
| oxadixyl | 0.005 | 1:3 | 5–10% |
| $Na_2HPO_3$ | 0.015 | | |
| metalaxyl | 0.02 | — | 30–50% |
| ofurace | 0.02 | — | >50% |
| oxadixyl | 0.02 | — | >50% |
| $Na_2HPO_3$ | 0.02 | — | 10–20% |

The concentration of a fungicide of group I, i.e. of an acylaniline, can be partly increased by one of the protective components listed at the outset. Microbicidal compositions which contain, as third optional component, copper sulfate, copper (oxy)chloride, zineb, maneb, propineb, mancozeb, folpet, captan, captafol, chlorothalonil, dithianone, dichlofuanide, chloroneb or hymexazole, also constitute an object of the present invention. The amount of the third component can be up to three times that of the acylaniline.

Typical examples are three-component mixtures based on metalaxyl, e.g. metalaxyl/folpet/phosphite or metalaxyl/chlorothalonil/phosphite.

(B)

Under the above described biological conditions for controlling Plasmopara viticola on vines, the following result is obtained with a three-component mixture of this kind (amount of Ia +Ib =amount of I).

| Test combination | Spray mixture | | Fungus attack on 7th day |
|---|---|---|---|
| | % by weight | Ratio I:II | |
| metalaxyl (Ia) | 0.002 | 2:5 | no visible attack |
| folpet (Ib) | 0.004 | | |
| $H_3PO_3$ | 0.015 | | |

(C) Action against Plasmopora viticola ("acylaniline resistant") on vines

Preventive and curative action

Vine cuttings in the 4-leaf stage are inoculated with a sporangia suspension of a Plasmopara strain that has diminished sensitivity to acylaniline fungicides such as metalaxyl, furalaxyl, ofurace, cyprofuram, oxadixyl (and comparable representatives). One day later, after onset of the disease, the vine cuttings are sprayed with a spray mixture prepared from a wettable powder formulation of the test compound or combination of test compounds (determination of curative action).

Two and six days after the first inoculation, a second and third inoculation with the sporangia suspension is made (determination of preventive action).

The temperature during the test is maintained at 20°–22 C. and the relative humidity is kept at 95–100%.

Three replicates were carried out for each compound (or combination) at its given concentration. Evaluation was made 11 and 15 days after the first inoculation. The following surprising potentiations of activity were obtained on combined treatment of the plants with a combination of an acylaniline of formula I and a salt of phosphorous acid (a.i.=active ingredient). 0 % activity=100% attack.

| Concentrations in ppm a.i. | | Activity (%) | |
|---|---|---|---|
| $Na_2HPO_3$ | Metalaxyl | after 11 days | after 15 days |
| 400 | — | 0 | 0 |
| — | 1000 | 96 | 96 |
| — | 250 | 92 | 92 |
| — | 60 | 72 | 68 |
| — | 15 | 20 | 20 |
| 400 | +1000 | 100 | 100 |
| 400 | +250 | 100 | 100 |
| 400 | +60 | 96 | 92 |
| 400 | +15 | 88 | 82 |

(D) Action against Plasmopara viticola ("acylaniline-resistant") on vines

Preventive and curative action

Metalaxyl and $H_3PO_3$ are tested in an assay similar to C, using a strain of Plasmopara viticola which is more sensitive to acylanilines than that used in (C). Evaluation was made 8 days after the first inoculation.

| Concentrations in ppm a.i. | | Activity (%) after incubation for 8 days |
|---|---|---|
| $H_3PO_3$ | Metalaxyl | |
| 2000 | — | 86 |
| 600 | — | 33 |
| — | 60 | 100 |
| — | 20 | 60 |
| 2000 | +20 | 100 |
| 600 | +60 | 100 |
| 600 | +20 | 100 |

What is claimed is:

1. A fungicidal composition comprising two active components, one component (a) of which is a compound of the formula

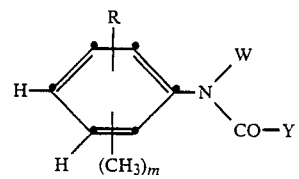

wherein
R is methyl,
W is the alpha-methylpropionate group,
Y is methoxymethyl, and
m is 1; and
the second component (b) of which is a phosphorous acid or a salt thereof containing at least one cation selected from the group consisting of alkali metals, alkaline earth metals, ammonium, zinc, copper, nickel and manganese, the weight ratio of (a):(b) being 1:100 to 1:1.

2. A composition according to claim 1, wherein the weight ratio of (a):(B) is 1:25 to 1:1.

3. A composition according to claim 2, wherein the weight ratio of (a):(b) is 1:8 to 1:1.5.

4. A composition according to claim 1 wherein the active component (b) is selected from the group consisting of
(a) $H_3PO_3$
(b) monosodium phosphite,
(c) monopotassium phosphite,
(d) disodium phosphite,
(e) dipotassium phosphite
(f) monoammonium phosphite,
(g) monobasic calcium phosphite,
(h) dibasic calcium phosphite,
(i) monobasic barium phosphite,
(j) dibasic barium phosphite,
(k) dibasic magnesium phosphite.
(l) dibasic zinc phosphite,
(m) dibasic copper(I) phosphite,
(n) dibasic copper(II) phosphite,
(o) dibasic nickel phosphite, and
(p) dibasic manganese phosphite.

5. A composition according to claim 4, wherein the active component (b) is selected from the group consisting of $H_3PO_3$, disodium phosphite, copper phosphite and calcium phosphite.

6. A composition according to claim 5, wherein the active component (a) is metalaxyl.

7. A composition according to claim 1, wherein the active component (a) is metalaxyl and the active component (b) is phosphorus acid or disodium phosphite.

8. A composition according to claim 7, wherein the weight ratio of (a):(b) is 1:25 to 1:4.

9. A method of controlling plant diseases at a locus, which method comprises treating the plant or a locus thereof with a fungicidally effective amount of a composition according to claim 1, the locus being treated with the two components in any order or simultaneously.

* * * * *